United States Patent [19]
De et al.

[11] Patent Number: 5,645,848
[45] Date of Patent: *Jul. 8, 1997

[54] CONTROLLED RELEASE COMPOSITION FOR ACTIVE SUBSTANCES INTO AN AQUEOUS MEDIUM

[75] Inventors: Nimai C. De, Rochester; Anil M. Salpekar, Pittsford, both of N.Y.

[73] Assignee: Bausch & Lomb Incorporated, Rochester, N.Y.

[*] Notice: The term of this patent shall not extend beyond the expiration date of Pat. No. 5,364,601.

[21] Appl. No.: 471,669

[22] Filed: Jun. 6, 1995

Related U.S. Application Data

[62] Division of Ser. No. 245,151, May 17, 1994, which is a continuation of Ser. No. 997,423, Dec. 28, 1992, abandoned.

[51] Int. Cl.⁶ .................................................. A01N 25/32
[52] U.S. Cl. ........................ 424/408; 422/30; 424/405; 424/406; 514/839; 514/840
[58] Field of Search ........................ 424/405, 94.4, 424/94.3, 408, 406; 134/901; 514/839, 840; 252/186.28; 422/28, 30; 435/177, 189

[56] References Cited

U.S. PATENT DOCUMENTS

| | | | |
|---|---|---|---|
| 3,912,451 | 10/1975 | Gaglia, Jr. | 21/158 |
| 4,568,517 | 2/1986 | Kaspar et al. | 422/30 |
| 4,585,488 | 4/1986 | Giefer | 134/27 |
| 4,748,992 | 6/1988 | Giefer | 134/84 |
| 4,767,559 | 8/1988 | Kruse et al. | 252/106 |
| 4,882,150 | 11/1989 | Kaufman | 424/428 |
| 4,976,921 | 12/1990 | Itagaki et al. | 422/28 |
| 5,008,106 | 4/1991 | Merianos et al. | 424/80 |
| 5,011,661 | 4/1991 | Schafer et al. | 422/30 |
| 5,145,644 | 9/1992 | Park et al. | 422/28 |
| 5,223,265 | 6/1993 | Wong | 424/473 |
| 5,338,480 | 8/1994 | Dziabo et al. | 252/187.21 |
| 5,362,647 | 11/1994 | Cook et al. | 435/264 |
| 5,364,601 | 11/1994 | Salpekar | 422/28 |
| 5,384,091 | 1/1995 | Rontome et al. | 422/30 |
| 5,447,650 | 9/1995 | Cafaro | 424/78.04 |
| 5,521,091 | 5/1996 | Cook et al. | 435/264 |
| 5,549,891 | 8/1996 | Sulc et al. | 424/94.4 |
| 5,556,480 | 9/1996 | Rontome et al. | 134/26 |

FOREIGN PATENT DOCUMENTS

| | | |
|---|---|---|
| 0 124 461 | 11/1984 | European Pat. Off. . |
| 89/00045 | 1/1989 | WIPO . |
| 90/11786 | 10/1990 | WIPO . |
| 91/16883 | 11/1991 | WIPO . |

*Primary Examiner*—John C. Bleutge
*Assistant Examiner*—Robert H. Harrison
*Attorney, Agent, or Firm*—Chris P. Konkol; Craig E. Larson

[57] ABSTRACT

A composition for delaying release of an active component into an aqueous fluid is taught which includes a capsule that swells in the presence of an aqueous fluid allowing moisture to enter the capsule into contact with a capsule decomposing agent activated by the entering moisture such that the agent decomposes the capsule sufficiently to release the active agent at a predetermined delayed time after the capsule contacts the aqueous fluid. A preferred capsule composition is gelatin and decomposing agents are a proteolytic enzyme or a salt that effects the osmotic gradient of the system. The controlled release composition of the invention is preferably utilized in a soft contact lens disinfecting system wherein a solution of hydrogen peroxide disinfects the lenses followed by neutralization of residual hydrogen peroxide wherein release of the neutralizing agent is delayed by means of the capsule proteolytic enzyme or salt composition.

12 Claims, No Drawings

CONTROLLED RELEASE COMPOSITION FOR ACTIVE SUBSTANCES INTO AN AQUEOUS MEDIUM

This is a divisional of application Ser. No. 08/245,151 filed on May 17, 1994, which in turn is a continuation of Ser. No. 07/997,423 filed on Dec. 28, 1992.

FIELD OF THE INVENTION

The invention relates to controlled release of an active component into an aqueous system. More particularly, the invention relates to controlled release of a reducing agent, such as catalase, into an aqueous oxidizing solution, such as $H_2O_2$ solution for disinfecting soft contact lenses, to neutralize residual oxidizing agent, $H_2O_2$.

BACKGROUND OF THE INVENTION

It is often desired to immediately introduce an active agent into a fluid system yet delay its reaction with components of the system until after some other desired result is achieved. The disinfecting of soft contact lenses with hydrogen peroxide and subsequent neutralization of residual $H_2O_2$ presents such a situation.

The use of hydrogen peroxide systems for disinfecting soft contact lenses is well known for its efficacy. Such a use requires that residual hydrogen peroxide remaining on the lenses after disinfecting must be neutralized or decomposed to a biologically inert state before the disinfected lenses may be placed on the eyes. Significant residual $H_2O_2$ remaining on the lenses results in eye irritation, generally manifested by stinging sensations.

A number of neutralizing or reducing agents are known in the art. For example, U.S. Pat. No. 3,912,451 teaches neutralizing residual hydrogen peroxide by contacting the disinfecting solution with lenses therein with a metal catalyst, such as platinum, that catalyzes decomposition. A difficulty with these catalytic metal systems is that an excessive, inconvenient amount of time is required to reduce the solution hydrogen peroxide residues to a safe level.

Other agents are known in the art for decomposing hydrogen peroxide at a faster, more convenient rate. Of particular interest is the use of an enzyme, such as catalase. For example, U.S. Pat. Nos. 4,748,992 and 4,585,488 teach sterilizing contact lenses with $H_2O_2$ and subsequently contacting the lenses with an isotonic solution of dissolved catalase, resulting in effective decomposition of residual $H_2O_2$ taking place within a few minutes.

In addition to the relative effectiveness of disinfecting/neutralizing chemicals per se, a major goal in designing lens care methods and formulations relates to simplifying their methods of use. It is widely accepted that regimens for disinfecting and cleaning contact lenses must be as simple as possible to encourage lens wearers to comply with the care regimens as a matter of avoiding adverse health effects due to contaminated lenses. Any simplification in a regimen, such as by combining processing steps, combining chemicals, or adding separate components at the same time, is generally advantageous in achieving patient compliance.

Simplifying lens care regimens by combining disinfecting and neutralizing components remains difficult to achieve because of the difficulty of balancing the relative reaction rates of the disinfecting and neutralizing processes. A difficulty with fast neutralizing of $H_2O_2$ systems, such as catalase, is that the lenses, to be effectively disinfected, must be exposed to a relatively high concentration of $H_2O_2$ for a significant, finite period of time in order to achieve disinfecting before neutralizing proceeds significantly. The time required for disinfection is generally dependent upon the concentration of hydrogen peroxide utilized, requiring on the order of two hours at 1.0 weight percent $H_2O_2$ while only five minutes at 3.0% by weight hydrogen peroxide.

Since it is preferred that $H_2O_2$ concentration be as low as possible, it is evident that if one desires to treat lenses simultaneously with hydrogen peroxide disinfectant and a fast acting neutralizion such as catalase, it is necessary to employ the neutralizer with care. In fact, it is preferable to delay the effective release of such a neutralizer, in order to allow for adequate time to achieve disinfecting and, thereafter, obtain substantially complete neutralization of the disinfecting hydrogen peroxide component.

A number of proposals have been made for delaying release of the neutralizing agent until after the disinfecting step is at least substantially complete. For example, Kruse, et al., in U.S. Pat. No. 4,767,559, form a one step cleaning/disinfecting tablet that includes an outer layer that is the disinfecting component and a core that comprises the neutralizing agent. The disinfecting agent may be any acid-reacting, $H_2O_2$-generating compound such as potassium persulfate, melamine perhydrate or, preferably, urea peroxhydrate. The core neutralizing agent comprises a reducing agent, such as ascorbic acid or glucose or an enzyme, such as catalase. In operation, the disinfecting agent first dissolves, then the core dissolves to neutralize the cleaning agent. A difficulty with this product is that the process for making such an outer layered/core tablet is complex which adds significant cost such that no commercial product has yet been successfully marketed using this concept.

Kaspar et al, in U.S. Pat. No. 4,568,517, describe simultaneously contacting lenses with a hydrogen peroxide solution and a neutralizing agent, preferably sodium thiosulfate or sodium sulfite, in a solid form such as a tablet. The neutralizer agent is provided with a coating which dissolves gradually to release neutralizer only after the disinfecting period has elapsed. The $H_2O_2$ solution transformed in situ into a buffered saline lens storage solution having a pH of 6.5–8.5 and a tonicity of 200–450 milliosmol per kg solution. A difficulty with the preferred sodium thiosulfate tablet is that it is very large in size, making this approach impractical.

A further difficulty with controlled release systems is that of providing adequate flexibility in release times and profiles, as well as good uniformity of release. Schafer et al., in U.S. Pat. No. 5,011,661, describes controlled release of neutralizing agent into a peroxide system through an insoluble, yet semi-permeable membrane coating or capsule. The membrane comprises various polymers and triacetin for controlling release. Park et al., in U.S. Pat. No. 5,145,644, describes a method of coating a tablet with a controlled release water soluble polymer employing a water and ketone solvent. The ketone containing solvent is said to produce increased uniformity of coating.

It is quite evident that improvements in controlled release products and methods are desirable that provide for increased flexibility and uniformity of delivery of an active agent into a aqueous system. The need is particularly evident for a delayed release composition and method that delivers a neutralizer such as catalase into a hydrogen peroxide disinfecting system such that the neutralizer is precisely timed and uniformly delivered wherein the disinfecting step is achieved without premature neutralization.

SUMMARY OF THE INVENTION

The invention is a composition for delaying release of an active component into an aqueous fluid. The composition comprises a capsule that swells in the presence of an aqueous fluid, allowing moisture to enter said capsule, and a capsule decomposing agent activated by said entering moisture, wherein said agent decomposes said capsule sufficiently to release said active component at a predetermined delayed time after said capsule contacts said aqueous fluid.

In a preferred composition, the capsule is formed of gelatin that is substantially insoluble in aqueous solution at ambient temperature.

The decomposing agent is a preferably proteolytic enzyme in an amount sufficient to achieve a predetermined release of active component. Alternatively, the decomposing agent is a water soluble inorganic or organic salt, such as sodium chloride in an amount sufficient to achieve a predetermined release of active component.

The composition of the invention is preferably utilized for delaying release of a neutralizing composition into a solution of hydrogen peroxide for disinfecting contact lenses, said composition comprising a gelatin capsule that swells in the solution allowing moisture to enter the capsule; and, a capsule decomposing agent activated by the entering moisture wherein the agent decomposes and/or disintegrates the capsule sufficiently to release said neutralizing component into the solution, wherein release of the neutralizer is delayed until after the disinfecting step is completed.

In a preferred system, the disinfecting composition into which a neutralizer composition of the invention is to be delivered is hydrogen peroxide solution, derived from any source. A preferred disinfecting source of $H_2O_2$ for use with the delayed release means for delivering the neutralizing component comprises a poly-vinylpyrrolidone-hydrogen peroxide (PVP-$H_2O_2$)complex wherein said complex is in a solid form having an $H_2O_2$ component in an amount sufficient for said disinfecting. The PVP-$H_2O_2$ complex in solid form may be combined with the solid encapsulated neutralizer, either within the capsule or as a separate dry component in a package. The two components are simultaneously placed in an aqueous medium in which the contact lenses are submerged. Disinfecting is accomplished by the $H_2O_2$ component present, followed by neutralizing of residual $H_2O_2$ that is delayed until after disinfecting is complete.

Preferably, the PVP-$H_2O_2$ complex comprises 5–40% by weight $H_2O_2$. The PVP-$H_2O_2$ complex is in the form of a solid tablet, granules or powder for combination with the neutralizer component in a dry package or capsule.

The means employed for delaying and controlling release of neutralizer comprises encapsulating the neutralizer component in a capsule that dissolves or disintegrates in the aqueous medium by action of a decomposing agent contained within the capsule at a rate sufficiently slow such that $H_2O_2$ efficacy is achieved prior to significant neutralization by the neutralizer. Preferably, the capsule comprises a gelatin that is insoluble but swells in aqueous solution at ambient temperature.

Preferably, the neutralizer component further comprises a capsule decomposing agent, a proteolytic enzyme within the capsule, wherein the capsule in the aqueous medium swells, transmitting sufficient water into the capsule to activate the proteolytic enzyme to digest the capsule, releasing the neutralizer into the aqueous medium whereby residual $H_2O_2$ is neutralized. Preferably, the proteolytic enzyme is subtilisin and the neutralizer is a catalase or peroxidase enzyme.

The invention includes adjusting the amount of subtilisin to adjustably delay digestion of the capsule to provide sufficient time for disinfecting by said PVP-$H_2O_2$ complex, wherein the amount of time delay necessary is determined by the concentration of the $H_2O_2$ disinfecting solution employed.

Alternatively, the neutralizer component comprises, as a capsule decomposing agent for delaying release of said active agent catalase enzyme, an inorganic salt, within said capsule, such as NaCl, KCl or mixtures thereof. Most preferably, the composition of the invention includes NaCl in an amount of about 5–106 milligrams per capsule wherein catalase release is substantially delayed for about 2–3 hours.

The invention also includes a method of disinfecting contact lenses, comprising submerging said lenses in an aqueous medium, adding to said aqueous medium a composition comprising poly-vinylpyrrolidone-hydrogen peroxide (PVP-$H_2O_2$) complex wherein said complex is in a solid form, having an $H_2O_2$ component in an amount sufficient for said disinfecting and adding substantially simultaneously with the disinfecting PVP-$H_2O_2$ complex, a neutralizer component, in a solid form, said neutralizer in an amount sufficient to substantially neutralize residual $H_2O_2$ from said disinfecting, said neutralizer component including means for delaying release and action of said neutralizer until after said disinfecting step.

The disinfecting solution holding the lenses, after neutralizing, is a hypertonic solution of greater than 350 milliosmols per kilogram solution. Thus, the method further comprises rubbing and rinsing the disinfected lenses with a preserved isotonic saline solution prior to insertion of said lenses in the eye.

DETAILED DESCRIPTION OF THE INVENTION

The invention is a means for delaying the effect or release of an active component into an aqueous fluid until after some other effect or processing step is substantially complete. The preferred means for delaying release comprises encapsulating the active component in a capsule that remains substantially intact for a sufficient period of time to allow the first desired effect to occur and then subsequently disintegrates sufficiently to allow release of the active component. The capsule is further characterized by swelling in the aqueous fluid such that an amount of moisture is transmitted into the capsule to activate an internal decomposing agent which after activation sufficiently destroys the integrity of the capsule to release the active ingredient.

A preferred delayed release means is provided by a gelatin capsule containing a proteolytic enzyme, as the decomposing agent, and the active agent. The gelatin capsule containing the above-noted ingredients, when introduced into an aqueous medium, softens and swells but remains substantially intact for sufficient time to allow the first processing step to proceed. A sufficient amount of moisture from the aqueous medium, however, penetrates the capsule to dissolve the proteolytic enzyme which causes its activation. The enzyme begins a digestion and decomposing process and, subsequently, disintegration of the gelatin capsule occurs, finally releasing the active agent to perform its function.

Alternative decomposing agents are water soluble salts that affect the osmotic gradient between the solution and the environment in the interior of the capsule. Thus, the presence of a salt such as NaCl in the capsule will encourage the flow of aqueous fluid into the capsule causing its disintegration.

The capsule may be made of any semipermeable material that remains intact in aqueous solution, passing moisture into the capsule at a delayed, desired rate wherein the moisture activates a decomposing agent or an agent of similar effect that causes sufficient destruction of the integrity of the capsule such that an active agent within the capsule is discharged into the aqueous solution. An alternative capsule material is starch with an internal decomposing agent of amylase.

It is well evident that the composition and method for delaying delivery of an active component into an aqueous fluid is useful for delivering any type of active ingredient into any system where the effect of the active component is to be delayed. Thus, delivery of any reducing agent into an aqueous oxidizing system, or vice versa, is within the scope of the invention. The delivery of a component designed to regulate an aqueous system in any way is within the scope of the delayed release or delayed delivery composition or method of the present invention.

A preferred system for utilization of this invention is for disinfecting soft contact lenses with a solution or other source of $H_2O_2$. The delayed active component in such a system is a neutralizing component for reducing $H_2O_2$ remaining in the disinfecting solution after disinfecting is complete. The following description of the invention focuses upon the contact lenses disinfecting process but is equally applicable to delayed delivery of any material into an aqueous system or solution.

A key element of the invention is controlling the rate of dissolution or decomposing of the gelatin capsule by utilizing a means that permits flexibility in establishing a desired release time, is precise in controlling release and is reliably uniform, capsule to capsule. The precise composition of the gelatin, chemical modification of the gelatin material wall, thicknesses of the capsule and other similar means are available and comtemplated for adjusting rate of release and profile of the release of active agent from the capsule. In the contact lens disinfecting/neutralizing system, the invention insures that substantially no neutralizing occurs during the disinfecting period, permitting use of lower concentration $H_2O_2$ solutions than the prior art systems.

A preferred means of regulating dissolution is to vary the concentration of proteolytic enzyme present within the capsule. This means is demonstrated in the examples below.

An additional means of regulating the rate of dissolution of the gelatin capsule and hence release of neutralizer is provided by selecting an appropriate water soluble inorganic or organic salt mixture and concentration. For example, inclusion of an amount of sodium chloride in an excipient mixture in the capsule provides a means of regulating disintegration time by effecting the osmotic gradient of the system. As demonstrated in the examples below, the presence of sodium chloride in the capsule within a range of about 10 to 100 milligrams per capsule has a profound effect upon release of neutralizer and, hence, residual concentration of $H_2O_2$ over time. By varying the concentration of sodium chloride, the neutralizer may be isolated from contact with the disinfecting solution for a substantial period of time and then suddenly released to neutralize the hydrogen peroxide. This characteristic release pattern is a distinct advantage in light of the requirement that disinfecting efficacy generally requires a certain concentration level for a definite period of time to be effective. The two means of controlling delayed release may be combined to achieve a desired effect.

The neutralizer component of the invention may have, as its active ingredient, any of a number of compositions that neutralize or decompose oxidizing agents and, particularly, hydrogen peroxide to non-irritating water and oxygen. Thus, the neutralizer component for the hydrogen peroxide system of particular interest may be sodium thiosulfate, thiourea, sodium sulfite, thio glycerol, sodium formate, ascorbic acid or the like.

The neutralizer may also be an enzyme in a powder form, most preferably, catalase. Catalase is conventionally obtained from beef liver or microbial sources and has a crystalline structure. It is prepared for the present invention in a dry form. The catalase enzyme will decompose conventional 3% hydrogen peroxide within moments of contact with the hydrogen peroxide containing solution. The careless component is particularly stable in its solid, substantially dry, form.

In a preferred combination, a gelatin capsule includes a catalase neutralizing agent for the delayed neutralization of residual $H_2O_2$ in aqueous solution in a contact lens disinfecting regimen. A preferred capsule decomposing enzyme is subtilisin A or NaCl or mixtures thereof. Other ingredients and excipients may also, of course, be included to ensure proper pH tonicity end the like.

The lenses to be disinfected are submerged in an aqueous medium that is preferably a saline solution. The solution is preferably preserved and may be isotonic or hypertonic. Other aqueous solutions may be used as desired so long as they are compatible with components of the invention.

The delayed release composition and method employed in the $H_2O_2$ contact lenses disinfecting system may utilize any source of $H_2O_2$ for disinfecting. A preferred $H_2O_2$ source is a solid complex formation of polyvinylpyrrolidone (PVP) and hydrogen peroxide ($H_2O_2$), as described by Merianos et al, in U.S. Pat. No. 5,008,106. It is an anhydrous, uniform, free flowing fine white powder which may be stably mixed with other components of the composition of the invention. The complex may be about 3–24% by weight $H_2O_2$. A preferred $H_2O_2$ content is 18–22% $H_2O_2$ and 1–2% $H_2O$.

Both the PVP-$H_2O_2$ and catalase neutralizer are in solid form which may be combined in a single package for simultaneous delivery into an aqueous medium for holding the contact lenses to be disinfected. The ingredients must be packaged in a manner that prevents any significant premature reaction between the active components. A preferred packaging includes the disinfectant in tablet or powder form and the neutralizer contained within a capsule, as described above. The preferred packaging may include a moisture proof foiled pouch containing all of the disinfecting and neutralizing components.

The following examples demonstrate the delayed release delivery composition of the invention, including utilization of the invention in contact lens disinfecting/neutralizing processes.

EXAMPLE 1

Efficacy of PVP-$H_2O_2$ Dissolved in Preserved Saline Solution

A preferred source of $H_2O_2$ disinfecting solution for contact lenses for use in combination with the delayed delivery system of the invention is a solid PVP-$H_2O_2$ complex. The PVP-$H_2O_2$ complex supplied by ISP Technologies, Inc. of Wayne, N.J., as a uniform, free flowing fine white powder, is 18–20% by weight $H_2O_2$ and 1–2% by weight $H_2O$. Sufficient amounts of said complex are dissolved in an isotonic saline solution, preserved with sorbic acid to form solutions having 0.5 to 3% by weight $H_2O_2$.

Test volumes containing $10^6$ organisms/volume concentrations of test microorganisms are prepared for *Candida* albicans (Ca), *Aspergilles fumagatus* (Af) and *S. marcescens* (Sm) using standard culture methods, harvest techniques and quantitative microbiological analysis. Table I demonstrates efficacy of the PVP-$H_2O_2$ complex described above.

TABLE I

| % $H_2O_2$ | | Log Reduction of | | | | | | |
|---|---|---|---|---|---|---|---|---|
| | | Sm | | Ca | | Af | | |
| [wt %] | pH | 1 hr | 4 hrs | 2 hr | 4 hrs | 1 hr | 2 hrs | 4 hrs |
| 3.0 | 5.9 | 1.7 | >4.5 | >4.4 | >4.4 | 2.4 | >4.9 | >4.9 |
| 2.0 | 6.1 | 1.1 | >4.5 | 2.9 | >4.4 | 1.3 | 3.4 | >4.9 |
| 1.0 | 6.5 | 0.8 | 2.3 | 1.2 | 1.9 | 0.4 | 0.6 | 2.3 |

EXAMPLE 2

Controlled Release of Encapsulated Neutralizer and Resulting Residual $H_2O_2$

The controlled release composition of the invention is a gelatin capsule and a decomposing agent comprising an enzyme or inorganic salt. A suitable gelatin capsule is manufactured by Capsagel, a division of Warner-Lambert Company of Greenwood, S.C. and characterized as Natual Conisnap®. The active agent delivered to the disinfecting solution of $H_2O_2$ is catalase, supplied by Sigma Chemical Co. of St. Louis, Mo., derived from bovine liver and is designated as Catalase EC 1.11.1.6. A mixture of catalase, subtilisin or NaCl and lactose filler (about 128 mg) is inserted into the gelatin capsule, in the amounts indicated in Table II.

The filled capsule is placed in an $H_2O_2$ solution generated by dissolving PVP-$H_2O_2$ solid in saline solution as described in Example 1 above. Table II reports residual $H_2O_2$ as a function of time(min).

TABLE II

| Release Controlling Agent | Conc. of Agent (mg) | Conc. of Catalase Neutralizer (mg) | Percent Remaining $H_2O_2$ v. time (min.) | | | | | |
|---|---|---|---|---|---|---|---|---|
| | | | 0 | 60 | 120 | 180 | 285 | 300 |
| a) subtilisin | 0.09 | 1.0 | 100 | 94.9 | 93.1 | ND | ND | 0 |
| b) NaCl | 70.00 | 1.4 | 100 | 44.1 | 27.0 | ND | ND | 0 |
| c) NaCl | 9.50 | 1.0 | 100 | 100.0 | — | 96.6 | 9.8 | ND |

Examples 2(b) and 2(c) demonstrate the effects that concentration of an inorganic salt decomposing agent has on the disinfecting environment. In Example 2(c) the concentration of NaCl is such that residual $H_2O_2$ remains substantially unaffected for about 180 minutes, before rapidly dropping to zero at about 285 minutes. In contrast, Example 2(b) shows a much faster release of neutralizer and rapid reduction of residual $H_2O_2$.

EXAMPLE 3

Effect of Concentration of Subtilisin-A Decomposing Agent on the Release of Neutralizer (PVP-$H_2O_2$ System)

TABLE III

| Time | Percent Remaining $H_2O_2$ (%) | | | | |
|---|---|---|---|---|---|
| (min) | A | B | C | D | E |
| 0 | 100 | 100 | 100 | 100 | 100 |
| 60 | 48.0 | 64.1 | 91.0 | 98.9 | 92.7 |
| 120 | 4.6 | 20.7 | 23.5 | 98.9 | 92.7 |
| 300 | 0 | 0 | 0 | 7.1 | ND |
| 360 | — | — | — | 0 | 0 |

A Gelatin capsule, size 4; catalase, 1 mg; sodium chloride, 11 mg; subtilisin-A, 1 mg of lactose; and lactose, 102 mg.
B The composition is the same as in A, except subtilisin-A is 0.44 mg of lactose per capsule.
C The composition is the same as in A except Subtilisin-A is 0.2 mg on lactose per capsule.
D The composition is the same as in A except there was no subtilisin-A in the capsule.
E Gelatin capsule, size 4; catalase, 1 mg; subtilisin-A, 0.08 mg on lactose, 130 mg.

EXAMPLE 4

The following example is substantially the same as Example 3 except that the source of $H_2O_2$ is a conventional aqueous 3% $H_2O_2$ solution rather than being derived from solid PVP-$H_2O_2$ complex.

TABLE IV

| Time | Percent Remaining $H_2O_2$ (%) Capsule | | |
|---|---|---|---|
| (min) | A | B | C |
| 0 | 100 | 100 | 100 |
| 20 | ND | ND | 89.0 |
| 30 | 89.5 | ND | ND |
| 60 | 0 | 56.7 | 0 |

TABLE IV-continued

| Time | Percent Remaining $H_2O_2$ (%) Capsule | | |
|---|---|---|---|
| (min) | A | B | C |
| 120 | — | 14.6 | — |
| 360 | — | 0 | — |

Capsule A: catalase, 1 mg; subtilisin A, 0.08 mg on lactose; and lactose 128 mg.
Capsule B: catalase, 1 mg; sodium chloride, 11 mg; and lactose, 128 mg
Capsule C: catalase, 1 mg; sodium chloride, 11 mg; subtilisin A, 0.2 mg on lactose; and lactose, 122 mg.

EXAMPLE 5

Efficacy of Controlled Release Disinfection System of the Invention

Gelatin capsules identified as "Capsule 12" and containing: catalase, 1 mg; subtilisin, 2 mg; and lactose, 137 mg, comprising the neutralizing component of the invention, are placed, substantially simultaneously with PVP-$H_2O_2$ complex, into a test sample of saline inoculated with the indicated test organism at a concentration of $10^6$ microorganisms/test volume. The samples are tested periodically over 6 hours for log reduction of microorganism population to determine efficacy.

TABLE V

*Candida Albicans* - Log Reduction of Organism Population vs Time [hrs]

| Sample | 1 hr | 2 hrs | 4 hrs | 6 hrs |
|---|---|---|---|---|
| Capsule 12 | 0.9 | 1.5 | 2.5 | 2.2 |

TABLE VI

*Aspergillus fumigatus* - Log Reduction of Organism Population

| | 1 hr | 2 hrs | 4 hrs | 6 hrs |
|---|---|---|---|---|
| Capsule 12 | 1.5 | 2.5 | 4.2 | 4.1 |

In operation, contact lenses to be disinfected are placed in an isotonic saline solution, preferably preserved. As a preferred source of $H_2O_2$, solid PVP-$H_2O_2$ and the delayed release capsule of the invention, including the encapsulated neutralizer, are added substantially simultaneously to the solution holding the lenses. The PVP-$H_2O_2$ dissolves, producing an $H_2O_2$ concentration of less than 3% by weight $H_2O_2$, preferably about 2% by weight $H_2O_2$ or less, which effectively disinfects the lenses. The required time for completion of disinfecting varies depending upon the concentration of the $H_2O_2$ and other factors. Water from the solution at ambient temperature (below 30° C.) causes the capsule, preferrably gelatin, to swell and a small amount of water is transmitted through the walls of the capsule into contact with the components therein. The water entering the capsule activates the capsule decomposing agents, i.e., proteolytic enzyme and/or inorganic salt present within the capsule, initiating disintegration of the capsule walls. Depending upon the excipients present within the capsule, the disintegration or decomposing process, and, hence, the releasing of neutralizing component, is delayed for a time sufficient to permit disinfection of the lenses. The neutralizer component, preferably catalase, is then released. The catalase within minutes begins to reduce the $H_2O_2$ level of the disinfecting solution and, ultimately, decomposition reduces the residual level to that which can be accommodated by the eye. The resulting solution is a hypertonic solution having an osmolality of greater than 350 milliosmols/kg solution. A rub and rinse of the lenses with isotonic saline is typically done before the lenses are inserted into the eye.

A preferred regimen is as follows:
1. Remove lenses from the eye
2. Rub and rinse with preserved saline
3. Place lenses in a lens holder
4. Transfer contents of the packets including the solid PVP-$H_2O_2$ complex and capsule to the lens holder
5. Add 10 cc of preserved saline
6. Place lenses in the lens holder
7. Allow to soak for up to 6 hours
8. Remove lenses and rinse with preserved saline before inserting in the eye It will be evident to those skilled in the art that the controlled release composition of the invention is useful for controlled release of any agent into an aqueous solution. Thus, the invention can be applied to acid-base redox and other applications where it is desired to introduce an active component into an aqueous medium but delay the effect of the active component for a preselected period of time.

We claim:

1. A composition for delayed release of a neutralizing component into a solution of hydrogen peroxide for disinfecting contact lenses, comprising:

a capsule that swells in said solution, allowing moisture to enter said capsule;

a neutralizing component within the capsule that is capable of neutralizing hydrogen peroxide; and a capsule decomposing agent within the capsule that is activated by the entering of said moisture to sufficiently decompose said capsule and release said neutralizing component into said solution;

wherein release of the neutralizing component is timed to occur after said disinfecting is completed, thereby neutralizing residual hydrogen peroxide.

2. The composition of claim 1 wherein said capsule is gelatin.

3. The composition of claim 2 wherein said capsule decomposing agent comprises a proteolytic enzyme, wherein the capsule swells in the solution, transmitting sufficient water into the capsule to activate the proteolytic enzyme to digest the capsule, thereby releasing the neutralizing component into the aqueous medium, whereby residual hydrogen peroxide is neutralized.

4. The composition of claim 3 wherein said proteolytic enzyme is subtilisin.

5. The composition of claim 3 wherein said neutralizing component is catalase.

6. The composition of claim 5 wherein the amount of subtilisin is adjusted to delay digestion of said capsule to provide sufficient time for disinfecting by said hydrogen peroxide solution.

7. The composition of claim 6 wherein said subtilisin is present in the amount of about 0.05 to 3.00 milligrams per capsule and the release of said catalase is substantially delayed for about 1 to 2 hours.

8. The composition of claim 1 wherein said means for delaying release of said neutralizing component comprises sodium chloride within said capsule.

9. The composition of claim 8 wherein said sodium chloride is present in said capsule in a range of about 5–100 milligrams per capsule.

10. The composition of claim 9 wherein said sodium chloride is present in said capsule in an amount of less than about 70 milligrams.

11. The composition of claim 8 wherein said sodium chloride is about 10 milligrams per capsule and the release of said catalase is substantially delayed for about 2–3 hours.

12. A composition for delayed release of a neutralizing component into a solution of hydrogen peroxide for disinfecting contact lenses, comprising:

a gelatin capsule that swells in said solution, allowing moisture to enter said capsule;

a neutralizing component within the capsule that is capable of neutralizing hydrogen peroxide;

a capsule decomposing agent within the capsule that is activated by the entering of said moisture to sufficiently decompose said capsule and release said neutralizing component into said solution;

wherein the release of the neutralizing component is timed to occur after said disinfecting is completed, thereby neutralizing residual hydrogen peroxide.

* * * * *